(12) United States Patent
Han et al.

(10) Patent No.: US 7,492,161 B2
(45) Date of Patent: Feb. 17, 2009

(54) NANOSIZED ELECTRICAL PROBE FOR MEASURING ELECTRICAL SIGNAL OF CHARGED COLLOIDAL PARTICLES, AND DEVICE OF MEASURING ELECTRICAL SIGNAL OF CHARGED COLLOIDAL PARTICLES USING THE SAME

(75) Inventors: Jin Han, Busan (KR); Na-Ri Kim, Busan (KR); Jae-Boum Youm, Busan (KR); Hyun Joo, Busan (KR); Dae-Young Hur, Busan (KR)

(73) Assignee: INJE University Industry—Academic Cooperation Foundation, Kimhae Kyungnam (KR)

( * ) Notice: Subject to any disclaimer, the term of this patent is extended or adjusted under 35 U.S.C. 154(b) by 270 days.

(21) Appl. No.: 11/306,150

(22) Filed: Dec. 16, 2005

(65) Prior Publication Data
US 2006/0185451 A1   Aug. 24, 2006

(30) Foreign Application Priority Data
Feb. 24, 2005   (KR)   ..................... 10-2005-0015248

(51) Int. Cl.
*G01N 27/021* (2006.01)
(52) U.S. Cl. ..................................... 324/446
(58) Field of Classification Search ............ None
See application file for complete search history.

(56) References Cited

U.S. PATENT DOCUMENTS 6,959,481 B2 * 11/2005 Moreland et al. .......... 29/592.1

OTHER PUBLICATIONS

Saviane et al, "the muscle chloride channel C1C-1 has a double-barreled appearance that is differentially affected . . . ", Mar. 1999, J. Gen, Physiol vol. 113, pp. 457-467.*
Duncan et al, "Rat brain p64H1, expression of a new member of the p64 chloride . . . ", Sep. 19, 1997, The journal of Biological Chemistry vol. 272, pp. 23880-23886.
Song et al, "The topology of VDAC as probed by biotin modification", Sep. 18, 1998, The Journal of Biological Chemistry vol. 273, pp. 24406-24411.
Gincel et al, "Calcium binding and translocation by the voltage-dependent anion channel a possible regulatory mechanism . . . ", 2001, Biochem. J. vol. 358, pp. 147-155.
Zhang et al, "Characteristic and superoxide-induced activation of reconstituted myocardial mitochondrial . . . ", Dec. 2001, Circulation Research, pp. 1177-1183.
Lohret et al, "Tim23, a protein import component of the mitochondrial inner membrane, is required . . . ", Apr. 21, 1997, The Journal of Cell Biology vol. 137, pp. 377-386.
Bahamonde et al, Plasma membrane voltage-dependent anion channel mediates . . . , Jun. 5, 2003, The Journal of Biological Chemistry, pp. 33284-33288.
Saviane et al, "The muscle chloride channel C1C-1 has a double-barreled appearance that is differentially affected . . . ", March, J. Gen, Physiol vol. 113, pp. 457-467.

* cited by examiner

*Primary Examiner*—Robert R Raevis
(74) *Attorney, Agent, or Firm*—IPLA P.A.; James E. Bame

(57) ABSTRACT

The current invention relates to a nanosized electrical probe for measuring an electrical signal of charged colloidal particles, and a device for measuring an electrical signal of charged colloidal particles using the same, thus exhibiting excellent effects on measurement of variations in internal charge or voltage of the charged colloidal particles (e.g., mitochondria) in a solution.

6 Claims, 4 Drawing Sheets

Scale bar: 20μm

Scale bar: 5μm

NANOSIZED ELECTRICAL PROBE FOR MEASURING ELECTRICAL SIGNAL OF CHARGED COLLOIDAL PARTICLES, AND DEVICE OF MEASURING ELECTRICAL SIGNAL OF CHARGED COLLOIDAL PARTICLES USING THE SAME

BACKGROUND OF THE INVENTION

1. Field of the Invention

The present invention relates to a nanosized electrical probe for measuring an electrical signal of charged colloidal particles, and a device for measuring an electrical signal of charged colloidal particles using the same.

2. Description of the Related Art

In general, ion channels function not only to determine the voltage of a cell membrane affecting the excitability of cells, but also to control the concentration of intracellular $Ca^{2+}$ participating in the bio-signal transmission in almost all the cells. Thus, ion channels are importantly regarded as means for finding how the cells operate as bio-signal sensors and reactors. In this regard, a patch-clamp technique, which was invented by Neher & Sakmann in 1981, is employed to record the operation of a single ion channel by applying mechanical and physicochemical stimuli to the cell while varying intracellular or extracellular environments according to the intention of an experimenter, and is thus receiving attention as a core of the field of cell biology (Hamil et al., 1981; Neher et al., 1992).

However, such a patch-clamp technique for recording ion channel currents in cell levels is disadvantageous because it cannot be applied to charged colloidal particles (e.g., mitochondria) having a diameter of about 1 μm, which float in a solution, and thus it is impossible to measure their electrical bio-signals.

SUMMARY OF THE INVENTION

Accordingly, the present invention has been made keeping in mind the above problems occurring in the prior art, and an object of the present invention is to provide a nanosized electrical probe having a diameter of ones of nm, suitable for use in measurement of variation in internal (or surface) electrical charges or voltage of charged colloidal particles in a solution.

Another object of the present invention is to provide a device for measuring an internal or surface electrical signal of charged colloidal particles.

In order to accomplish the above objects, the present invention provides a nanosized electrical probe for measuring an electrical signal of charged colloidal particles, which is fabricated from a quartz capillary and has a diameter of 50~100 nm.

In addition, the present invention provides a device for measuring an electrical signal of charged colloidal particles, comprising the nanosized electrical probe of the present invention, a patch-clamp amplifier, and a chamber.

DESCRIPTION OF THE PREFERRED EMBODIMENTS

Figure 1A:
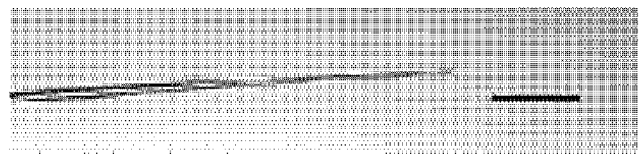
FIGS. 1A and 1B illustrate a conventional electrical probe and a nanosized electrical probe of the present invention, respectively.

Hereinafter, a detailed description will be given of the present invention, with reference to the appended drawings.

The present invention provides a nanosized electrical probe for measuring an electrical signal of charged colloidal particles, which is fabricated from a quartz capillary and has a diameter of 50~100 nm.

The nanosized electrical probe is fabricated using the quartz capillary. In addition, as an energy source required to fabricate the nanosized electrical probe, a laser heat source is preferably used. As such, any laser heat source may be used as long as it is known in the art. Thus, the nanosized electrical probe having a tip diameter of 50~100 nm is fabricated using the laser heat source.

Since a conventional electrical probe is fabricated using amorphous borosilicate glass and a low-temperature heat source, it is difficult to manufacture the tip thereof to have a diameter not larger than 5~10 μm.

However, in the present invention, the quartz capillary and the laser heat source, able to locally provide a high temperature to a target, are used. That is, a high-temperature laser heat source is applied to quartz comprising a layered molecular array while pulling both ends of the quartz, thus changing the layered molecular array of quartz into a monolayered level due to slip between the molecular layers, resulting in an electrical probe having a more precise and smaller diameter.

The nanosized electrical probe preferably has tip resistance of 100~150 MΩ when filled with an electrolytic solution. As such, various electrolytic solutions may be used. Even though a mitochondria-containing solution is introduced into the nanosized electrical probe filled with the electrolytic solution, two solutions are immiscible with each other, which is well known in the art in consideration of the very precise tip diameter of the nanosized electrical probe of the present invention.

In addition, the present invention provides a device for measuring an electrical signal of charged colloidal particles, which comprises the nanosized electrical probe of the present invention, a patch-clamp amplifier, and a chamber. As such, the electrical signal is recorded using the patch-clamp amplifier according to a cell-attached patch mode and an excised patch mode of a patch-clamp technique.

Preferably, the electrical signal measuring device of the present invention further includes a positively charged metal plate and a negatively charged metal plate therein, which are positioned at opposite side surfaces facing each other. Thereby, the nanosized electrical probe may be easily directed toward the charged colloidal particles (preferably, mitochondria). In general, negatively charged mitochondria of −200 mV are collected around the positively charged metal plate.

In the mitochondria, which are exemplified by the charged colloidal particles, the electrical signal of mitochondria may be measured through the inner membrane of mitochondria having ion channels in a state of the gigaseal of 10~100 GΩ being formed between the nanosized electrical probe and the inner membrane of mitochondria.

Moreover, according to the present invention, the mitochondria floating in a solution can be immobilized, one of which can be then selected and can easily come into contact with the nanosized electrical probe.

Preferably, the charged colloidal particles used in the present invention are mitochondria. The mitochondria, typically represented by the charged particles in the solution, are spherical particles having a diameter of 1 µm or less, and have electrical properties which vary from one moment to the next with intracellular signal transmission procedures between bio-active materials and the exchange of ion material with extracellular environments.

Research into signal transmission mechanisms of mitochondria has been mainly conducted to date using molecular biological and cell biological methods through cytochrome C and proteins regarding a cell killing mechanism.

In order to understand the signal transmission mechanism of mitochondria through ion channel proteins or receptor proteins present on the surface of mitochondria, the variation in electrical signals of mitochondria should be determined by selecting one mitochondrion and then measuring the internal or surface electrical signal of such a mitochondrion. Conventionally, however, the electrical signal is very difficult to directly measure due to the difficulty in fabricating a nanosized electrical probe.

In contrast, the present invention enables the measurement of the variation in an internal electrical signal or surface charge (or voltage) of the selected mitochondrion or similar charged colloidal particle. That is, the method of the present invention is used to measure the electrical bio-signal of mitochondria (or colloidal organelle) having a diameter of about 1 µm, and is a technique for directing the electrical probe toward the mitochondria, in particular, for minimizing the Brownian movement of mitochondria floating in the solution. Hence, the electrical bio-signal can be measured even in mitochondria having a diameter of about 1 µm, to which a patch-clamp technique is difficult to conventionally apply.

A better understanding of the present invention may be obtained in light of the following examples which are set forth to illustrate, but are not to be construed to limit the present invention.

EXAMPLE 1

Fabrication of Nanosized Electrical Probe for Measuring Electrical Signal of Charged Colloidal Particles A nanosized electrical probe was fabricated using a laser heat source and a quartz capillary having an inner diameter of 1.0 mm. As the laser heat source, a laser-based micropipette puller (P-2000, available from Sutter Instrument) was used.

Figure 1B:
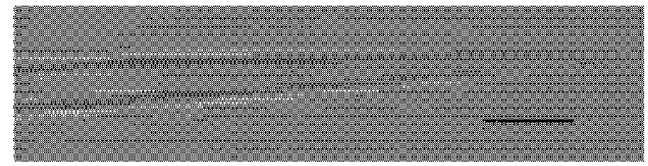

With the aid of the quartz capillary and the laser heat source able to locally provide a high temperature to a target, a high-temperature laser heat source was applied to quartz comprising a layered molecular array while pulling both ends of the quartz, thus changing the layered molecular array of quartz into a monolayered level due to slip between the molecular layers. Thereby, electrical probes having more precise and smaller diameters (tip diameter: 50~100 nm) were variously fabricated (FIG. 1A is a conventional electrical probe made of borosilicate glass and FIG. 1B is a nanosized electrical probe of the present invention).

EXAMPLE 2

Figure 2:
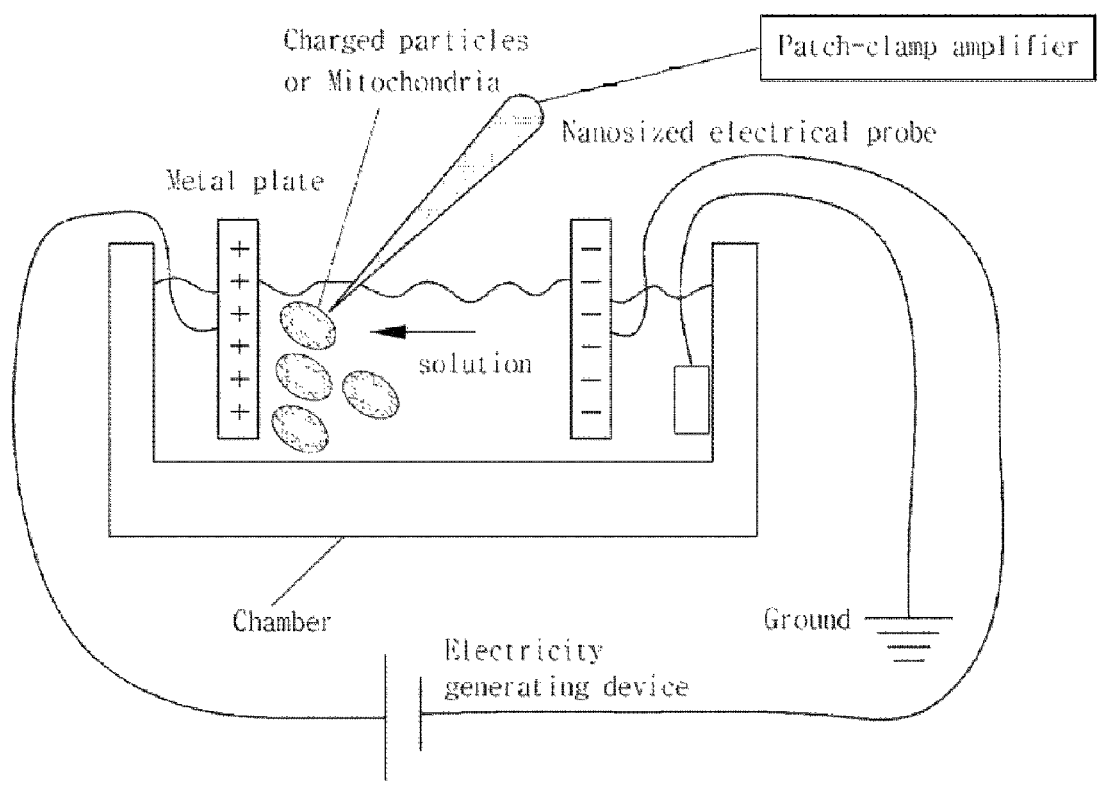
FIG. 2 schematically illustrates a device for measuring an electrical signal of mitochondria, according to the present invention.

Fabrication of Device for Measuring Electrical Signal of Mitochondria comprising Nanosized Electrical Probe and Patch-Clamp Amplifier A device for measuring the electrical signal of mitochondria was fabricated using the nanosized electrical probe fabricated in Example 1, a patch-clamp amplifier, positively and negatively charged metal plates, and a chamber (FIG. 2).

The nanosized electrical probe was filled with an NaCl solution to set the tip resistance thereof to 100 MΩ. The electrical signal was recorded using the patch-clamp amplifier according to a cell-attached patch mode and an excised patch mode of a patch-clamp technique.

The charged metal plate was used to easily direct the nanosized electrical probe toward the mitochondria. That is, negatively charged mitochondria of −200 mV were collected around the positively charged metal plate.

Figure 3:
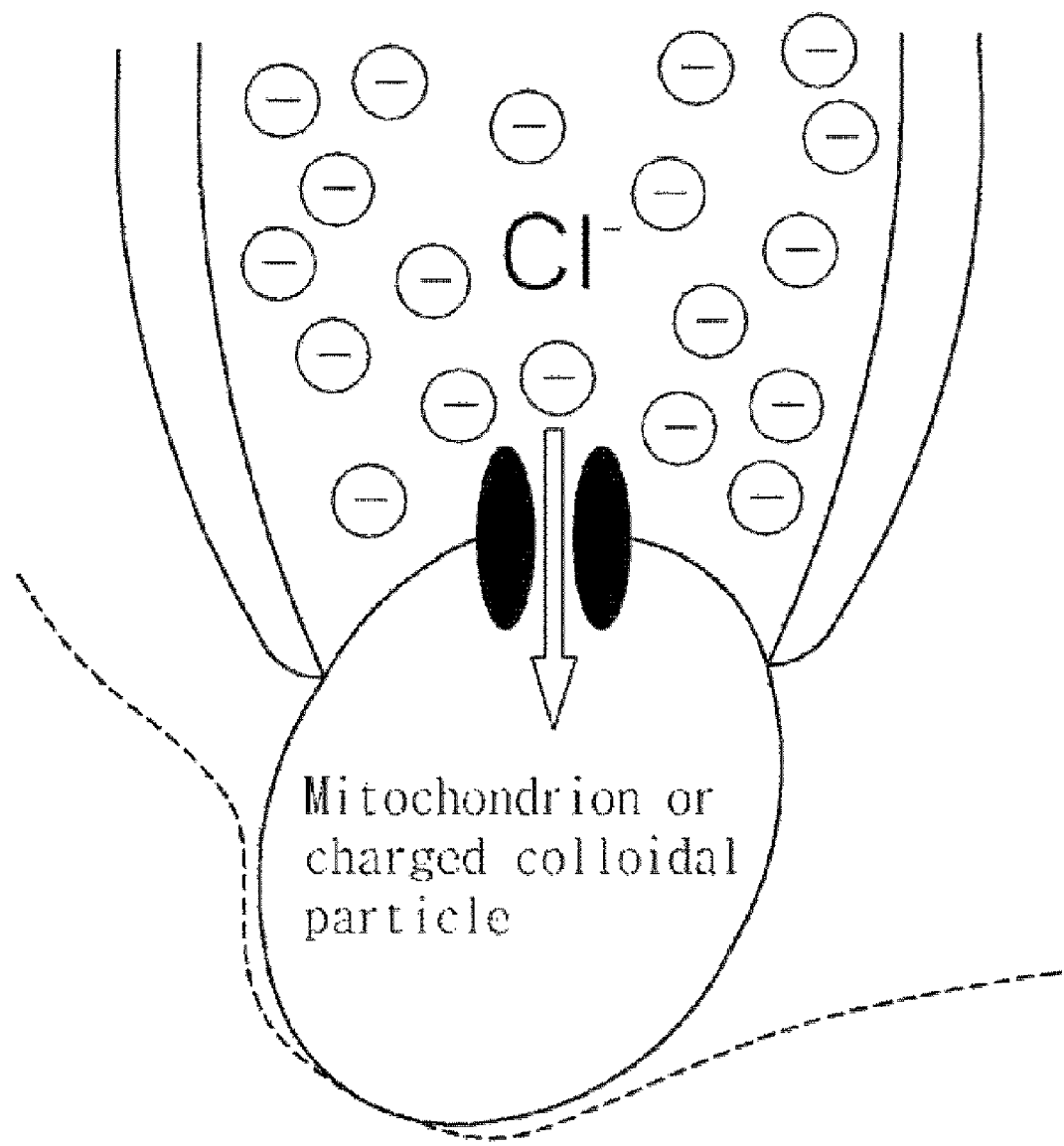
FIG. 3 illustrates a process of measuring an internal or surface electrical signal of one mitochondrion in a solution selected using the nanosized electrical probe of the present invention.

As the gigaseal of about 10~100 GΩ was formed between the nanosized electrical probe and the inner membrane of mitochondria, the electrical signal of the mitochondria was measured through the inner membrane of one mitochondrion having an ion channel (FIG. 3).

In particular, the mitochondria floating in a solution were immobilized, one of which was then selected and easily came into contact with the nanosized electrical probe.

EXAMPLE 3

Figure 4:
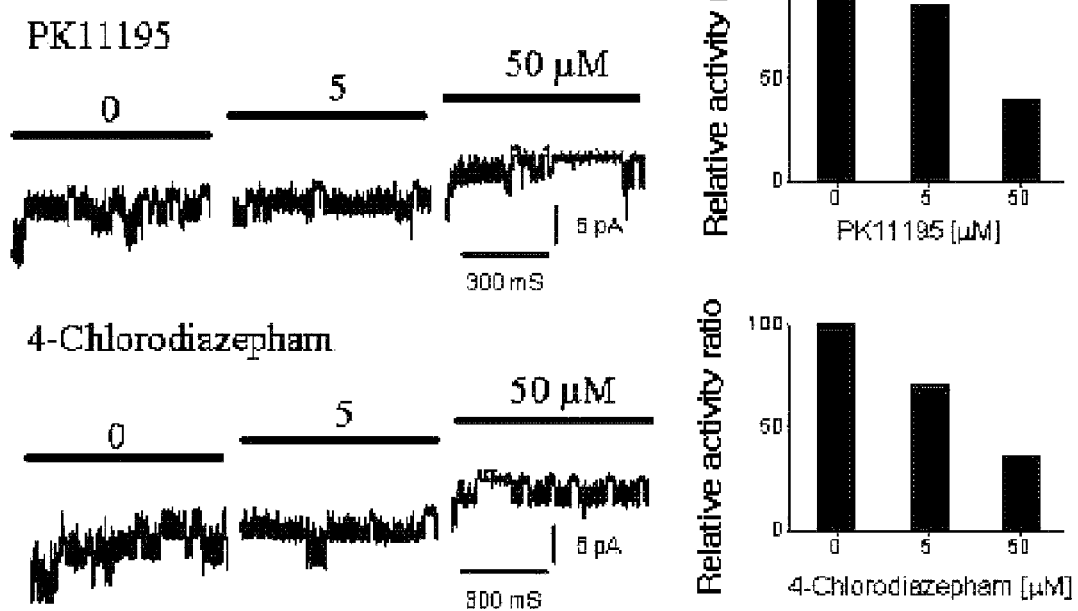
FIG. 4 illustrates a graph showing the variation in electrical signals of mitochondria recorded using the process of the present invention.

Measurement of Electrical Signal of Mitochondria Using Electrical Signal Measuring Device The electrical signal of mitochondria was recorded using the device fabricated in Example 2. The results are shown in FIG. 4. After mitochondria were transferred into the chamber disclosed in Example 2, the electrical signal was recorded using the patch-clamp technique. The experiment was conducted at room temperature, and a flow rate of experimental solution was controlled to 0.5 ml/min.

As shown in FIG. 4, the activity of an inner membrane anion channel (IMAC) present in the inner membrane of mitochondria was assayed by adding PK11195 and 4-chlorodiazepham to the solution in the chamber and then measuring the variation in internal electrical signals of mitochondria in the solution every hour using the techniques for fabricating a nanosized electrical probe and for immobilizing mitochondria.

As the result, the activity of IMAC was confirmed to be inhibited when adding PK11195 and 4-chlorodiazepham as an inhibitor of a peripheral benzodiazepine receptor (PBR) to the solution (FIG. 4). On the other hand, when an antagonist to the inhibitor was added, the activity of IMAC and the voltage of mitochondria were converted into their respective original states (not shown).

As is apparent from FIG. 4, when PK11195 and 4-chlorodiazepham were added, the internal electrical signals of mitochondria were varied, and recorded different peaks. Thus, the relative activity ratio of IMAC was found to vary with the amounts of the above two materials that were added.

Therefore, PBR was confirmed to be a participant in the activity of IMAC proposed as a novel signal transmission channel.

Thereby, it can be seen that the electrical signal of mitochondria is measured using the techniques for fabricating a nanosized electrical probe and for immobilizing mitochondria invented by the present inventors.

As previously described herein, the present invention provides a nanosized electrical probe for measuring an electrical signal of charged colloidal particles, and a device and method of measuring an electrical signal of charged colloidal particles using the same. According to the present invention, the variation in internal electrical charges or voltage of charged colloidal particles (e.g., mitochondria) in the solution can be measured. Therefore, the electrical probe, the device, and the method of measuring the electrical signal of charged colloidal particles of the present invention are suitable for use in the field of biotechnology, including mitochondria.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A nanosized electrical probe for measuring an electrical signal of charged colloidal particles, which is fabricated from a quartz capillary and has a tip diameter of 50~100 nm, wherein the nanosized electrical probe is filled with an electrolytic solution, and thus has a tip resistance of 100 to 150 Mohms.

2. The electrical probe as set forth in claim 1, wherein the nanosized electrical probe is fabricated using a laser heat source.

3. The electrical probe as set forth in claim 1, wherein the charged colloidal particles are mitochondria.

4. A nanosized electrical probe for measuring an electrical signal of charged colloidal particles, which is fabricated from a quartz capillary and has a tip diameter of 50~100 nm, wherein the nanosized electrical probe is filled with an electrolytic solution, and thus has a tip resistance of 100 to 150 Mohms, and wherein the nanosized electrical probe is connected to a patch-clamp amplifier.

5. The electric probe as set forth in claim 4, wherein the charged colloidal particles are mitochondria.

6. The electric probe as set forth in claim 4, wherein the patch-clamp amplifier operates in a cell-attached patch mode and an excised patch mode of a patch-clamp technique.

* * * * *